United States Patent
Watanabe

(10) Patent No.: US 11,141,049 B2
(45) Date of Patent: Oct. 12, 2021

(54) MEDICAL IMAGE PROCESSING SYSTEM, ENDOSCOPE SYSTEM, DIAGNOSTIC SUPPORT APPARATUS, AND MEDICAL SERVICE SUPPORT APPARATUS

(71) Applicant: FUJIFILM Corporation, Tokyo (JP)

(72) Inventor: Hiroki Watanabe, Kanagawa (JP)

(73) Assignee: FUJIFILM Corporation, Tokyo (JP)

(*) Notice: Subject to any disclaimer, the term of this patent is extended or adjusted under 35 U.S.C. 154(b) by 433 days.

(21) Appl. No.: 16/115,528

(22) Filed: Aug. 28, 2018

(65) Prior Publication Data
US 2019/0059707 A1    Feb. 28, 2019

(30) Foreign Application Priority Data
Aug. 29, 2017 (JP) .............................. JP2017-163979

(51) Int. Cl.
*A61B 1/00* (2006.01)
*A61B 5/1459* (2006.01)
(Continued)

(52) U.S. Cl.
CPC ...... *A61B 1/00186* (2013.01); *A61B 1/00009* (2013.01); *A61B 1/05* (2013.01);
(Continued)

(58) Field of Classification Search
CPC .............. A61B 1/0005; A61B 1/00186; A61B 5/14535; A61B 5/1459; A61B 5/4842; A61B 5/1032; A61B 5/1455
See application file for complete search history.

(56) References Cited

U.S. PATENT DOCUMENTS

| 4,110,604 | A | * | 8/1978 | Haynes | ............... G01N 15/1227 |
| | | | | | 377/10 |
| 5,631,165 | A | * | 5/1997 | Chupp | .................. B01F 5/0453 |
| | | | | | 422/63 |

(Continued)

FOREIGN PATENT DOCUMENTS

| JP | H01167664 | 7/1989 |
| JP | 2016050931 | 4/2016 |

(Continued)

OTHER PUBLICATIONS

"Search Report of Europe Counterpart Application", dated Feb. 18, 2019, p. 1-p. 16.

(Continued)

*Primary Examiner* — Alexandra L Newton
*Assistant Examiner* — Jae Woo
(74) *Attorney, Agent, or Firm* — JCIPRNET

(57) ABSTRACT

In order to support determination of a disease stage, there are provided a medical image processing system, an endoscope system, a diagnostic support apparatus, and a medical service support apparatus for reliably acquiring an index value relevant to visibility with respect to the state of red blood cells or the degree of irregularity of a gland duct structure according to the disease stage determination accuracy desired by a doctor. A light source unit emits a plurality of illumination light beams having different wavelength bands and different visibilities for red blood cells. An image acquisition unit acquires a plurality of medical images corresponding to respective illumination light beams by imaging an observation target illuminated with the respective illumination light beams. A red blood cell index value acquisition unit acquires a red blood cell index value, which is obtained by indexing the visibility of red blood cells, from each of the medical images.

7 Claims, 8 Drawing Sheets

(51) Int. Cl.
*A61B 1/06* (2006.01)
*A61B 5/00* (2006.01)
*A61B 1/05* (2006.01)
*A61B 5/145* (2006.01)
*G06T 7/00* (2017.01)
*A61B 5/103* (2006.01)
*A61B 5/02* (2006.01)

(52) U.S. Cl.
CPC .......... *A61B 1/0638* (2013.01); *A61B 1/0684* (2013.01); *A61B 5/1459* (2013.01); *A61B 5/14535* (2013.01); *A61B 5/4842* (2013.01); *G06T 7/0012* (2013.01); *A61B 1/0005* (2013.01); *A61B 5/02007* (2013.01); *A61B 5/1032* (2013.01); *A61B 5/489* (2013.01); *G06T 2207/10024* (2013.01); *G06T 2207/10068* (2013.01)

(56) References Cited

U.S. PATENT DOCUMENTS

| | | | | |
|---|---|---|---|---|
| 5,830,147 | A * | 11/1998 | Feke | A61B 3/1233 600/479 |
| 6,178,346 | B1 * | 1/2001 | Amundson | A61B 5/0086 348/77 |
| 8,203,709 | B2 * | 6/2012 | Ishii | A61B 5/418 356/326 |
| 10,022,074 | B2 * | 7/2018 | Shigeta | A61B 5/1459 |
| 10,113,966 | B2 * | 10/2018 | Yamada | G01N 33/49 |
| 10,426,318 | B2 * | 10/2019 | Kamon | A61B 1/00 |
| 10,653,295 | B2 * | 5/2020 | Ebata | A61B 5/1459 |
| 10,921,252 | B2 * | 2/2021 | Kaneko | A61B 1/00 |
| 2004/0030220 | A1 * | 2/2004 | Hamm | A61B 1/126 600/156 |
| 2004/0059215 | A1 * | 3/2004 | Nishimura | G16H 15/00 600/410 |
| 2005/0165279 | A1 | 7/2005 | Adler et al. | |
| 2008/0262313 | A1 * | 10/2008 | Shimizu | A61B 1/041 600/160 |
| 2011/0077870 | A1 * | 3/2011 | Linssen | G01N 15/147 702/19 |
| 2011/0124031 | A1 * | 5/2011 | Hazen | G01N 33/6893 435/29 |
| 2012/0176486 | A1 * | 7/2012 | Maeda | G01J 3/10 348/68 |
| 2013/0010094 | A1 | 1/2013 | Satish et al. | |
| 2014/0100427 | A1 * | 4/2014 | Saito | A61B 5/14503 600/178 |
| 2014/0221794 | A1 * | 8/2014 | Yamaguchi | A61B 1/0646 600/322 |
| 2014/0319379 | A1 * | 10/2014 | Manian | G01N 21/6428 250/459.1 |
| 2015/0366444 | A1 | 12/2015 | Morimoto et al. | |
| 2016/0331282 | A1 * | 11/2016 | Satish | A61B 5/02042 |
| 2018/0055372 | A1 * | 3/2018 | Watanabe | A61B 1/00009 |
| 2018/0082104 | A1 * | 3/2018 | Wan | G06K 9/0014 |
| 2018/0168490 | A1 * | 6/2018 | Jones | A61B 5/7282 |
| 2018/0206738 | A1 * | 7/2018 | Kamon | A61B 1/00188 |
| 2018/0211385 | A1 * | 7/2018 | Imai | A61B 1/00 |
| 2018/0218499 | A1 * | 8/2018 | Kamon | A61B 5/0084 |
| 2019/0073769 | A1 * | 3/2019 | Watanabe | A61B 5/4842 |
| 2019/0187125 | A1 * | 6/2019 | Otani | G01N 21/6428 |
| 2019/0239737 | A1 * | 8/2019 | Aoyama | A61B 1/00 |
| 2019/0254509 | A1 * | 8/2019 | Aoyama | A61B 1/00009 |
| 2019/0374088 | A1 * | 12/2019 | Watanabe | A61B 1/0052 |
| 2020/0046267 | A1 * | 2/2020 | Govari | A61B 5/02007 |

FOREIGN PATENT DOCUMENTS

| | | |
|---|---|---|
| JP | 2016067706 | 5/2016 |
| JP | 2017070504 | 4/2017 |
| WO | 2017057572 | 4/2017 |

OTHER PUBLICATIONS

"Office Action of Japan Counterpart Application", dated Sep. 23, 2020, with English translation, p. 1-p. 7.

* cited by examiner

FIG. 3
| FIRST ILLUMINATION LIGHT (410nm) | Invisible | Visible | Visible |
|---|---|---|---|
| SECOND ILLUMINATION LIGHT (450nm) | Invisible | Invisible | Visible |
| | 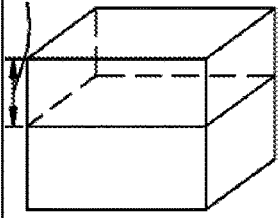 | 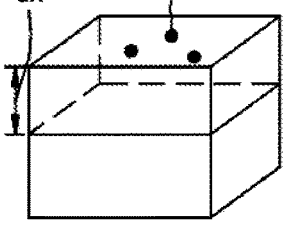 RED BLOOD CELL | 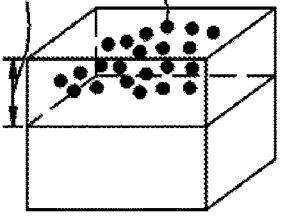 RED BLOOD CELL |
FIG. 4
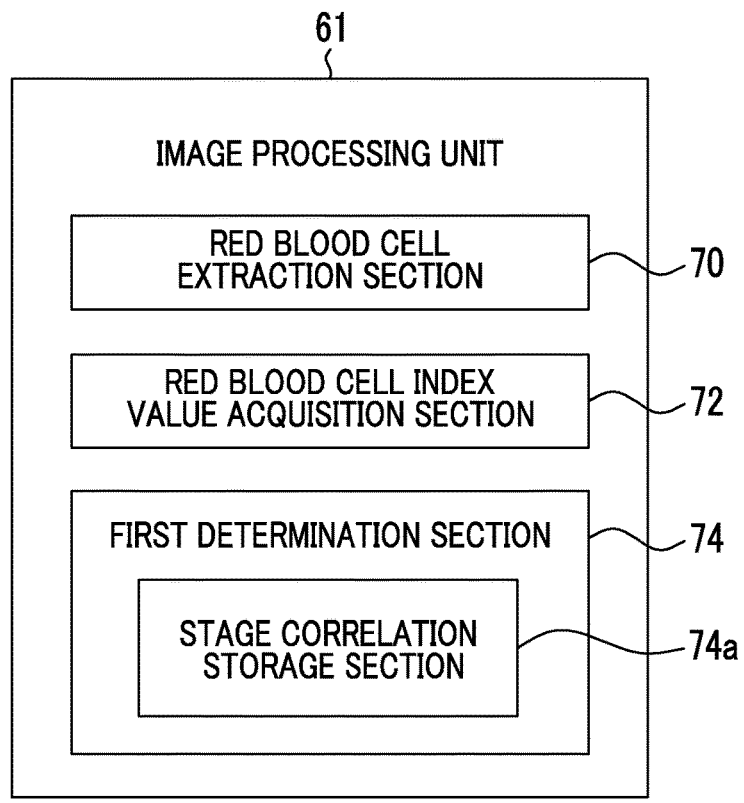

|  | DISEASE STAGE | | |
| --- | --- | --- | --- |
|  | Mayo0 | Mayo1 | Mayo2 |
| FIRST RED BLOOD CELL INDEX VALUE | 0 | 1 | 1 |
| SECOND RED BLOOD CELL INDEX VALUE | 0 | 0 | 1 |

| FIRST ILLUMINATION LIGHT (410nm) | Visible | Visible | Invisible |
|---|---|---|---|
| SECOND ILLUMINATION LIGHT (450nm) | Visible | Invisible | Invisible |
| | GLAND DUCT STRUCTURE | GLAND DUCT STRUCTURE | GLAND DUCT STRUCTURE |

|  | DISEASE STAGE | | |
|---|---|---|---|
|  | Mayo0 | Mayo1 | Mayo2 |
| FIRST GLAND DUCT STRUCTURE INDEX VALUE | 1 | 1 | 0 |
| SECOND GLAND DUCT STRUCTURE INDEX VALUE | 1 | 0 | 0 |

MEDICAL IMAGE PROCESSING SYSTEM, ENDOSCOPE SYSTEM, DIAGNOSTIC SUPPORT APPARATUS, AND MEDICAL SERVICE SUPPORT APPARATUS

CROSS-REFERENCE TO RELATED APPLICATIONS

The present application claims priority under 35 U.S.C. § 119 to Japanese Patent Application No. 2017-163979, filed on Aug. 29, 2017. Each of the above application(s) is hereby expressly incorporated by reference, in its entirety, into the present application.

BACKGROUND OF THE INVENTION

1. Field of the Invention

The present invention relates to a medical image processing apparatus, an endoscope system, a diagnostic support apparatus, and a medical service support apparatus for acquiring various index values used to examine an observation target.

2. Description of the Related Art

In the current medical field, medical image processing systems using medical images are widespread in the examination of observation targets. Among the medical image processing systems, in an endoscope system, an endoscope image that is one of medical images is acquired by emitting illumination light to an observation target and imaging the observation target. The acquired endoscope image is displayed on a display unit, such as a monitor, and is used to examine the observation target.

In addition, in recent years, various index values have been acquired from endoscope images and used to examine observation targets. For example, JP2017-70504A discloses that a plurality of blood vessel index values relevant to blood vessels are acquired under a plurality of different observation conditions, such as observation distances, and blood vessel parameters obtained by combining these blood vessel index values are used for determination of the state of an observation target, such as disease stage and type.

SUMMARY OF THE INVENTION

In JP2017-70504A, blood vessel index values or blood vessel parameters relevant to blood vessels are used for determination of the state of the observation target. However, a doctor determines the state of the observation target by referring to features other than blood vessels in many cases. For example, in inflammatory bowel disease, it is known that floating of red blood cells due to bleeding or the like occurs and the affected part has a high blood concentration as the disease stage progresses. Accordingly, the doctor determines the disease stage by referring to the state of red blood cells. It is also known that as the disease stage progresses, the degree of irregularity of a gland duct structure, such as a pit pattern, increases. Accordingly, the doctor determines the disease stage by referring to the degree of irregularity of the gland duct structure.

As described above, in the case of determining the disease stage by referring to the state of red blood cells or the degree of irregularity of the gland duct structure, the determination result is influenced by the degree of experience or the degree of proficiency of the doctor in many cases. In order to objectively determine the disease stage without being influenced by the degree of experience or the degree of proficiency of the doctor as described above, it is necessary to index the degree of irregularity of the gland duct structure or red blood cells and support the determination of the disease stage based on the indexed value. In order to support the determination of such a disease stage, it is required to reliably acquire an index value relevant to visibility with respect to the state of red blood cells or the degree of irregularity of the gland duct structure according to the disease stage determination accuracy desired by the doctor.

In order to support determination of a disease stage, it is an object of the invention to provide a medical image processing system, an endoscope system, a diagnostic support apparatus, and a medical service support apparatus for reliably acquiring an index value relevant to visibility with respect to the state of red blood cells or the degree of irregularity of a gland duct structure according to the disease stage determination accuracy desired by a doctor.

A medical image processing system of the invention comprises: a light source unit that emits a plurality of illumination light beams having different wavelength bands and different visibilities for red blood cells; an image acquisition unit that acquires a plurality of medical images corresponding to respective illumination light beams by imaging an observation target illuminated with the respective illumination light beams; and a red blood cell index value acquisition unit that acquires a red blood cell index value, which is obtained by indexing the visibility of red blood cells, from each of the medical images.

It is preferable to further comprise a first determination unit that determines a state of the observation target from the red blood cell index value with reference to a correlation between the state of the observation target and the red blood cell index value. It is preferable that the plurality of illumination light beams include first illumination light having a center wavelength of 410 nm and second illumination light having a center wavelength of 450 nm, the red blood cell index value acquisition unit acquires a first red blood cell index value from a medical image corresponding to the first illumination light, and acquires a second red blood cell index value from a medical image corresponding to the second illumination light, and the first determination unit determines that there is no precipitation amount of the red blood cells in a case where both the first red blood cell index value and the second red blood cell index value indicate that the red blood cells are not visually recognizable, determines that the precipitation amount of the red blood cells is equal to or less than a specific value in a case where the first red blood cell index value indicates that the red blood cells are visually recognizable and the second red blood cell index value indicates that the red blood cells are not visually recognizable, and determines that the precipitation amount of the red blood cells exceeds the specific value in a case where both the first red blood cell index value and the second red blood cell index value indicate that the red blood cells are visually recognizable.

It is preferable that the plurality of illumination light beams include first illumination light having a center wavelength of 410 nm and second illumination light having a center wavelength of 450 nm, the red blood cell index value acquisition unit acquires a first red blood cell index value from a medical image corresponding to the first illumination light, and acquires a second red blood cell index value from a medical image corresponding to the second illumination light, and the first determination unit determines the state of the observation target based on a third red blood cell index value obtained by weighting the first red blood cell index value and the second red blood cell index value and adding up the weighted first red blood cell index value and the weighted second red blood cell index value.

A medical image processing system of the invention comprises: a light source unit that emits a plurality of illumination light beams having different wavelength bands and different visibilities for a degree of irregularity of a gland duct structure; an image acquisition unit that acquires a plurality of medical images corresponding to respective illumination light beams by imaging an observation target illuminated with the respective illumination light beams; and a gland duct structure index value acquisition unit that acquires a gland duct structure index value, which is obtained by indexing the visibility with respect to the degree of irregularity of the gland duct structure, from each of the medical images.

It is preferable to further comprise a second determination unit that determines a state of the observation target from the gland duct structure index value with reference to a correlation between the state of the observation target and the gland duct structure index value. It is preferable that the plurality of illumination light beams include first illumination light having a center wavelength of 410 nm and second illumination light having a center wavelength of 450 nm, the gland duct structure index value acquisition unit acquires a first gland duct structure index value from a medical image corresponding to the first illumination light, and acquires a second gland duct structure index value from a medical image corresponding to the second illumination light, and the second determination unit determines a first disease stage in a case where both the first gland duct structure index value and the second gland duct structure index value indicate that the degree of irregularity of the gland duct structure is visually recognizable, determines a second disease stage in which a disease state is worse than in the first disease stage in a case where the first gland duct structure index value indicates that the degree of irregularity of the gland duct structure is visually recognizable and the second gland duct structure index value indicates that the degree of irregularity of the gland duct structure is not visually recognizable, and determines a third disease stage in which the disease state is worse than in the second disease stage in a case where both the first gland duct structure index value and the second gland duct structure index value indicate that the degree of irregularity of the gland duct structure is not visually recognizable.

It is preferable that the plurality of illumination light beams include first illumination light having a center wavelength of 410 nm and second illumination light having a center wavelength of 450 nm, the gland duct structure index value acquisition unit acquires a first gland duct structure index value from a medical image corresponding to the first illumination light, and acquires a second gland duct structure index value from a medical image corresponding to the second illumination light, and the second determination unit determines the state of the observation target based on a third gland duct structure index value obtained by weighting the first gland duct structure index value and the second gland duct structure index value and adding up the weighted first gland duct structure index value and the weighted second gland duct structure index value.

An endoscope system of the invention comprises: a light source unit that emits a plurality of illumination light beams having different wavelength bands and different visibilities for red blood cells; an endoscope that emits any one of the plurality of illumination light beams to an observation target; an image acquisition unit that acquires a plurality of medical images corresponding to respective illumination light beams by imaging the observation target illuminated with the respective illumination light beams; and a red blood cell index value acquisition unit that acquires a red blood cell index value, which is obtained by indexing the visibility of red blood cells, from each of the medical images.

An endoscope system of the invention comprises: a light source unit that emits a plurality of illumination light beams having different wavelength bands and different visibilities for a degree of irregularity of a gland duct structure; an endoscope that emits any one of the plurality of illumination light beams to an observation target; an image acquisition unit that acquires a plurality of medical images corresponding to respective illumination light beams by imaging the observation target illuminated with the respective illumination light beams; and a gland duct structure index value acquisition unit that acquires a gland duct structure index value, which is obtained by indexing the visibility with respect to the degree of irregularity of the gland duct structure, from each of the medical images.

A diagnostic support apparatus of the invention comprises the medical image processing system of the invention described above. A medical service support apparatus of the invention comprises the medical image processing system of the invention described above.

According to the invention, in order to support the determination of the disease stage, it is possible to reliably acquire an index value relevant to visibility with respect to the state of red blood cells or the degree of irregularity of the gland duct structure according to the disease stage determination accuracy desired by the doctor.

BRIEF DESCRIPTION OF THE DRAWINGS

FIG. 3 is an explanatory diagram showing the visibility of red blood cells with respect to first illumination light and second illumination light.

FIG. 4 is a block diagram showing a function of an image processing unit of a first embodiment.

DESCRIPTION OF THE PREFERRED EMBODIMENTS

First Embodiment

Figure 1:
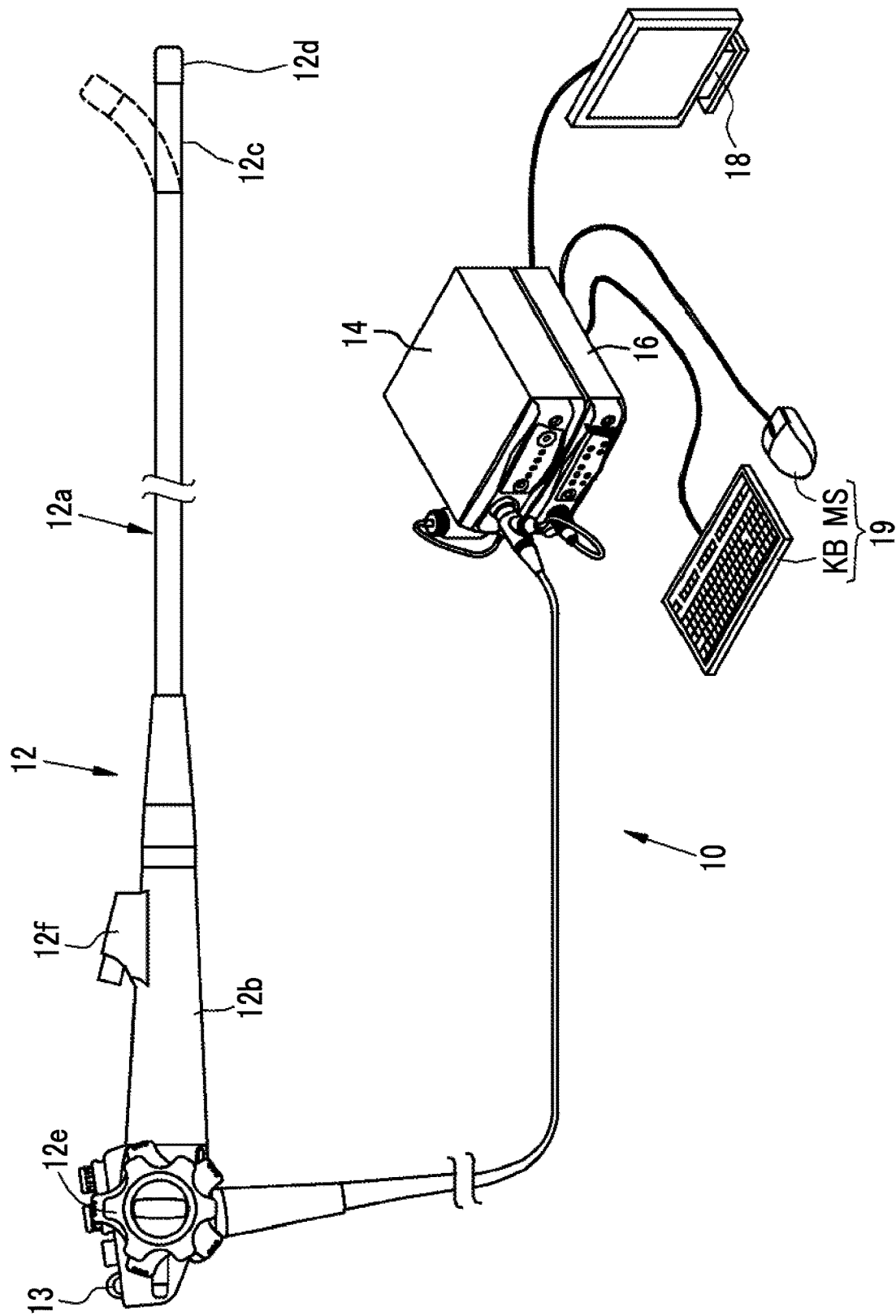
FIG. 1 is an external view of an endoscope system.

As shown in FIG. 1, an endoscope system 10 includes an endoscope 12, a light source device 14, a processor device 16, a monitor 18, and a user interface 19. The endoscope 12 emits illumination light to an observation target, and images the observation target irradiated with the illumination light. The light source device 14 generates illumination light to be emitted to the observation target. The processor device 16 performs system control of the endoscope system 10, image processing, and the like. The monitor 18 is a display unit that displays an image output from the processor device 16. The user interface 19 is an input device for performing a setting input or the like with respect to the processor device 16 and the like, and is configured to include a keyboard KB, a mouse MS, and the like.

The endoscope 12 has an insertion part 12a that is inserted into a subject, an operation unit 12b provided in a proximal end portion of the insertion part 12a, and a bending portion 12c and a distal end portion 12d that are provided on the distal end side of the insertion part 12a. By operating an angle knob 12e of the operation unit 12b, the bending portion 12c is bent. By the bending of the bending portion 12c, the distal end portion 12d faces in a desired direction. An injection port (not shown) for injecting air, water, or the like toward the observation target is provided in the distal end portion 12d.

In addition to the angle knob 12e, a zoom operation unit 13 is provided in the operation unit 12b. By operating the zoom operation unit 13, the observation target can be enlarged or reduced to capture an image. A forceps channel (not shown) for inserting a treatment instrument and the like is provided from the insertion part 12a to the distal end portion 12d. The treatment instrument is inserted into the forceps channel from a forceps inlet 12f.

Figure 2:
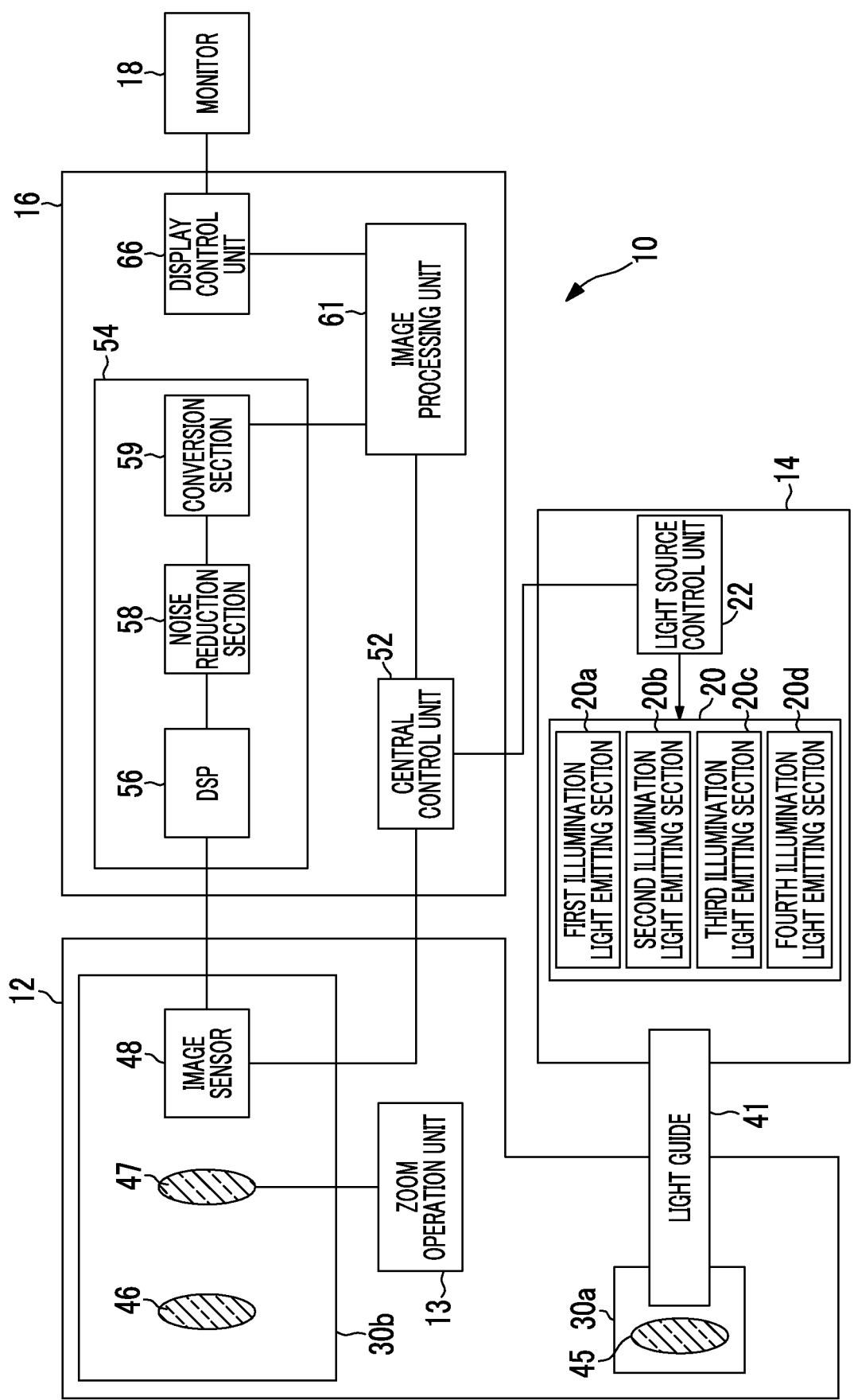
FIG. 2 is a block diagram of the endoscope system.

As shown in FIG. 2, the light source device 14 includes a light source unit 20 and a light source control unit 22. The light source unit 20 emits illumination light for illuminating the observation target. The light source unit 20 includes one or a plurality of light sources. Specifically, the light source unit 20 has first illumination light emitting section 20a that emits first illumination light having a center wavelength of 410 nm, a second illumination light emitting section 20b that emits second illumination light having a center wavelength of 450 nm, third illumination light emitting section 20c that emits third illumination light in a green band, and fourth illumination light emitting section 20d that emits fourth illumination light in a red band.

The light source control unit 22 controls the driving of the light source unit 20. The light source control unit 22 independently controls the timing of turning on or off each light source provided in the light source unit 20, the light emission amount at the time of lighting, and the like. As a result, the light source unit 20 can emit a plurality of kinds of illumination light beams having different light emission amounts or different emission timings. In the light source device 14, as emission modes for controlling the light emission of the light source unit 20, there are a normal mode in which all of the first illumination light, the second illumination light, the third illumination light, and the fourth illumination light are emitted and a special mode in which two or more illumination light beams, among the first illumination light, the second illumination light, the third illumination light, and the fourth illumination light, are automatically switched and emitted according to a specific light emission pattern. The special mode includes a red blood cell observation mode in which red blood cells contained in the observation target are observed by emitting the first illumination light and the second illumination light so as to be switched therebetween.

In the red blood cell observation mode, the visibility of red blood cells is different between a case where the observation target is illuminated with the first illumination light and a case where the observation target is illuminated with the second illumination light. As shown in FIG. 3, in a case where there is no precipitation amount of red blood cells in the observation target or a case where there is almost no precipitation amount of red blood cells, red blood cells are not visually recognized ("Invisible") in a case where any of the first illumination light and the second illumination light is emitted to the observation target. As in a case where the precipitation amount of red blood cells is small in the observation target, in a case where the precipitation amount of red blood cells is equal to or less than a specific value, red blood cells can be visually recognized ("Visible") in a case where the first illumination light is emitted to the observation target. On the other hand, in a case where the second illumination light is emitted, red blood cells cannot be visually recognized ("Invisible"). As in a case where the precipitation amount of red blood cells is medium in the observation target, in a case where the precipitation amount of red blood cells exceeds a specific value, red blood cells can be visually recognized ("Visible") in a case where any of the first illumination light and the second illumination light is emitted to the observation target.

There is a correlation between the above-described visibility of red blood cells and the state of the observation target, such as ulcerative colitis or inflammatory bowel disease. Therefore, the visibility of red blood cells is indexed as a red blood cell index value, and the red blood cell index value is used for determination of the state of the observation target. FIG. 3 shows that red blood cells float within the range of depth "dx" from the mucosal surface.

As shown in FIG. 2, the illumination light emitted from the light source unit 20 is incident on a light guide 41. The light guide 41 is built into the endoscope 12 and a universal cord (not shown), and propagates the illumination light to the distal end portion 12d of the endoscope 12. The universal cord is a cord for connecting the endoscope 12 with the light source device 14 and the processor device 16. As the light guide 41, it is possible to use a multi-mode fiber. As an example, it is possible to use a small-diameter fiber cable having a diameter of ϕ0.3 mm to ϕ0.5 mm that includes a core with a diameter of 105 μm, a cladding with a diameter of 125 μm, and a protective layer as an outer skin.

An illumination optical system 30a and an imaging optical system 30b are provided in the distal end portion 12d of the endoscope 12. The illumination optical system 30a has an illumination lens 45, and illumination light is emitted to the observation target through the illumination lens 45. The imaging optical system 30b has an objective lens 46, a zoom lens 47, and an image sensor 48. The image sensor 48 images the observation target using reflected light (including scattered light, fluorescence emitted from the observation target, fluorescence due to medicine administered to the observation target, or the like in addition to the reflected light) of the illumination light that returns from the observation target through the objective lens 46 and the zoom lens 47.

The zoom lens 47 is moved by operating the zoom operation unit 13, thereby enlarging or reducing the observation target imaged by using the image sensor 48. In the red blood cell observation mode, the enlargement magnification of the observation target is set so that red blood cells can be visually recognized even in a case where the precipitation amount of red blood cells is medium. For example, in a case where the monitor 18 is 19 inches, it is preferable to set the enlargement magnification of the subject to be larger than "100 times". In a case where the red blood cell observation mode is set, it is preferable to automatically switch to an enlargement magnification at which red blood cells can be visually recognized. The automatic switching of the enlargement magnification may be performed in a gland duct structure observation mode of a second embodiment.

The image sensor 48 is, for example, a color sensor having primary color system color filters, and includes three kinds of pixels of a blue pixel (B pixel) having a blue color filter, a green pixel (G pixel) having a green color filter, and a red pixel (R pixel) having a red color filter. The blue color filter mainly transmits purple to blue light. The green color filter mainly transmits green light. The red color filter mainly transmits red light. In a case where the observation target is imaged using the primary color system image sensor 48 as described above, a maximum of three types of images of a blue image (B image) obtained from the B pixel, a green image (G image) obtained from the G pixel, and a red image (R image) obtained from the R pixel can be obtained at the same time.

As the image sensor 48, it is possible to use a charge coupled device (CCD) sensor or a complementary metal oxide semiconductor (CMOS) sensor. Although the image sensor 48 of the present embodiment is a primary color system color sensor, it is also possible to use a complementary color system color sensor. For example, the complementary color system color sensor has a cyan pixel in which a cyan color filter is provided, a magenta pixel in which a magenta color filter is provided, a yellow pixel in which a yellow color filter is provided, and a green pixel in which a green color filter is provided. Images obtained from the pixels of the respective colors described above in the case of using the complementary color system color sensor can be converted into a B image, a G image, and an R image by performing complementary color-primary color conversion. Instead of the color sensor, a monochrome sensor in which no color filter is provided can be used as the image sensor 48. In this case, by sequentially imaging the observation target using the illumination light of respective colors, such as BGR, it is possible to obtain images of the respective colors described above.

The processor device 16 has a central control unit 52, an image acquisition unit 54, an image processing unit 61, and a display control unit 66. The central control unit 52 performs overall control of the endoscope system 10, such as synchronous control of illumination light emission timing and imaging timing. In the case of inputting various settings using the user interface 19 or the like, the central control unit 52 inputs the input various settings to each unit of the endoscope system 10, such as the light source control unit 22, the image sensor 48, or the image processing unit 61.

The image acquisition unit 54 acquires the captured image of the observation target from the image sensor 48. Since the image acquired by the image acquisition unit 54 is an image obtained by a medical apparatus, such as the endoscope 12, the image is referred to as a medical image. The image acquisition unit 54 has a digital signal processor (DSP) 56, a noise reduction section 58, and a conversion section 59, and performs various kinds of processing on the acquired medical image using these as necessary. The DSP 56 performs various kinds of processing, such as defect correction processing, offset processing, gain correction processing, linear matrix processing, gamma conversion processing, demosaic processing, and YC conversion processing, on the acquired medical image as necessary.

The defect correction processing is processing for correcting the pixel value of each pixel corresponding to the defective pixel of the image sensor 48. The offset processing is processing for setting an accurate zero level by reducing a dark current component from the image subjected to the defect correction processing. The gain correction processing is processing for adjusting the signal level of each image by multiplying the image subjected to the offset processing by the gain. The linear matrix processing is processing for improving the color reproducibility of the image subjected to the offset processing, and the gamma conversion processing is processing for adjusting the brightness or the saturation of the image after the linear matrix processing.

In a case where the image sensor 48 is a color sensor, demosaic processing is performed. The demosaic processing (also referred to as isotropic processing or simultaneous processing) is processing for interpolating the pixel values of missing pixels, and is performed on the image after the gamma conversion processing. The missing pixel is a pixel having no pixel value due to the arrangement of color filters (since pixels of other colors are arranged in the image sensor 48). For example, since the B image is an image obtained by imaging the observation target in the B pixel, a pixel at a position corresponding to the G pixel or the R pixel has no pixel value. The demosaic processing is for generating the pixel values of pixels at the positions of the G and R pixels of the image sensor 48 by interpolating the B image. The YC conversion processing is processing for converting the image after the demosaic processing into a brightness channel Y, a color difference channel Cb, and a color difference channel Cr.

The noise reduction section 58 performs noise reduction processing on the brightness channel Y, the color difference channel Cb, and the color difference channel Cr using, for example, a moving average method or a median filter method. The conversion section 59 reconverts the brightness channel Y, the color difference channel Cb, and the color difference channel Cr after the noise reduction processing into images of the respective colors of BGR.

The image processing unit 61 performs various kinds of image processing on the medical image acquired by the image acquisition unit 54. In the image processing unit 61, types of image processing performed in the normal mode and the special mode are different. In the red blood cell observation mode, a red blood cell index value is calculated from the medical image, and the state of the observation target is determined based on the red blood cell index value. Details of the red blood cell observation mode will be described later. The display control unit 66 converts the medical image transmitted from the image processing unit 61, the observation state determination result, or the like into a format suitable for display on the monitor 18, and outputs the conversion result to the monitor 18. As a result, the medical image, the observation state determination result, or the like is displayed on the monitor 18.

As shown in FIG. 4, the image processing unit 61 includes a red blood cell extraction section 70, a red blood cell index value acquisition section 72, and a first determination section 74 used in the red blood cell observation mode. The red blood cell extraction section 70 extracts first red blood cells from the medical image obtained at the time of emission of the first illumination light. For the extraction of first red blood cells, it is preferable to binarize the medical image. For the binarized medical image, it is preferable to perform filtering processing for extracting spherical shapes in order to extract only spherical red blood cells and not to extract things other than red blood cells, such as linear blood vessels. Similarly, second red blood cells are extracted from the medical image obtained at the time of emission of the second illumination light. The extraction of the second red blood cells is also performed in the same manner as the extraction of the first red blood cells.

The red blood cell index value acquisition section 72 acquires a first red blood cell index value relevant to the visibility of the first red blood cells from the first red blood cells extracted by the red blood cell extraction section 70. The first red blood cell index value is set to two stages of "1" and "0". "1" is a case where the number of first red blood cells is equal to or greater than a predetermined value and the first red blood cells can be visually recognized by the user. "0" is a case where the number of first red blood cells is less than the predetermined value and the first red blood cells cannot be visually recognized by the user. Similarly, the red blood cell index value acquisition section 72 acquires a second red blood cell index value, which is obtained by indexing the precipitation amount of second red blood cells, from the second red blood cells extracted by the red blood cell extraction section 70. The method of acquiring the second red blood cell index value is the same as in the case of the first red blood cell index value.

The first determination section 74 determines the state of the observation target based on the first red blood cell index value and the second red blood cell index value acquired by the red blood cell index value acquisition section 72. The first determination section 74 determines the disease stage of ulcerative colitis as the state of the observation target. The disease stage of ulcerative colitis includes three stages of Mayo0 with no or almost no precipitation of red blood cells, Mayo1 with a small precipitation amount of red blood cells, and Mayo2 with a remarkable precipitation amount of red blood cells.

The correlation between the disease stage and the first red blood cell index value and the correlation between the disease stage and the second red blood cell index value are as follows. As shown in (A) of FIG. 5, the first red blood cell index value indicated by the solid line is "0" in the case of Mayo0, and is "1" in the case of Mayo1 and Mayo2. Therefore, only two stages of Mayo0 and Mayo1, 2 can be determined with the first red blood cell index value. As shown in (B) of FIG. 5, the second red blood cell index value indicated by the dotted line is "0" in the case of Mayo0 and Mayo1, and is "1" in the case of Mayo2. Therefore, only two stages of Mayo0, 1 and Mayo2 can be determined with the second red blood cell index value.

Figures 5, 6:
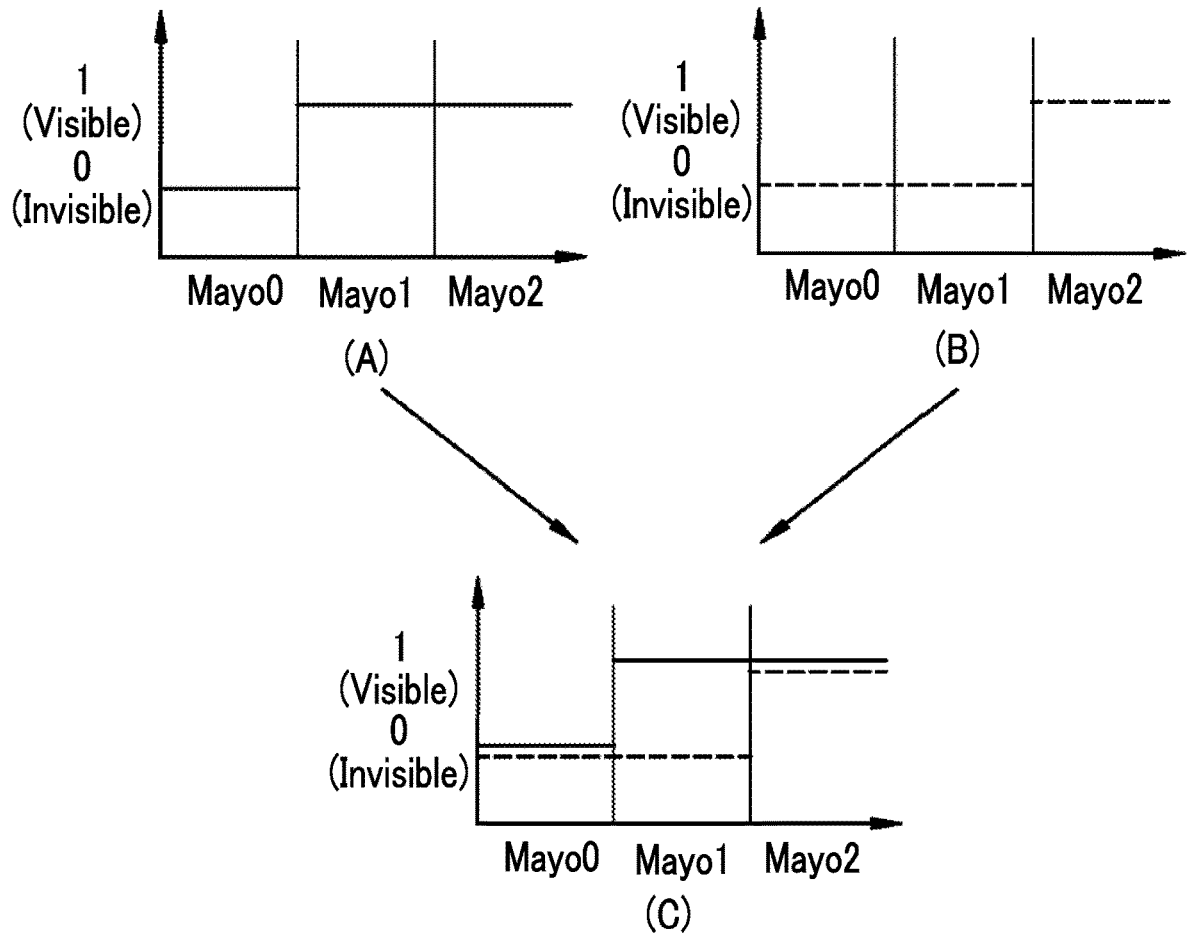
FIG. 5 is an explanatory diagram showing a correlation between the disease stage and a first red blood cell index value, a correlation between the disease stage and a second red blood cell index value, and a correlation between the disease stage and the first and second red blood cell index values.
FIG. 6 is a table showing a stage correlation table in which the correlation between the disease stage and each of the first red blood cell index value and the second red blood cell index value is stored.

Therefore, as shown in (C) of FIG. 5, Mayo1, 2, 3 can be determined in three steps by using both the first red blood cell index value and the second red blood cell index value. That is, in a case where both the first red blood cell index value and the second red blood cell index value are "0", Mayo0 is determined. In a case where the first red blood cell index value is "1" and the second red blood cell index value is "0", Mayo1 is determined. That is, in a case where both the first red blood cell index value and the second red blood cell index value are "1", Mayo2 is determined. From the above, it is possible to increase the resolution of the disease stage by using a plurality of red blood cell index values based on a plurality of illumination light beams having different visibilities for red blood cells, such as the first illumination light or the second illumination light. In this manner, in a case where the resolution of the disease stage with respect to illumination light to be used is known, it is possible to adjust the number of illumination light beams according to the determination accuracy of the disease stage desired by the doctor.

As shown in FIG. 6, the first determination section 74 includes a stage correlation table 74a in which the above-described correlation between the disease stage and each of the first red blood cell index value and the second red blood cell index value is stored. For example, in a case where the first red blood cell index value is "1" and the second red blood cell index value is "0", the first determination section 74 determines that the disease stage is "Mayo1" with reference to the stage correlation table 74a. The determination result is transmitted to the display control unit 66 and displayed on the monitor 18.

Figure 7:
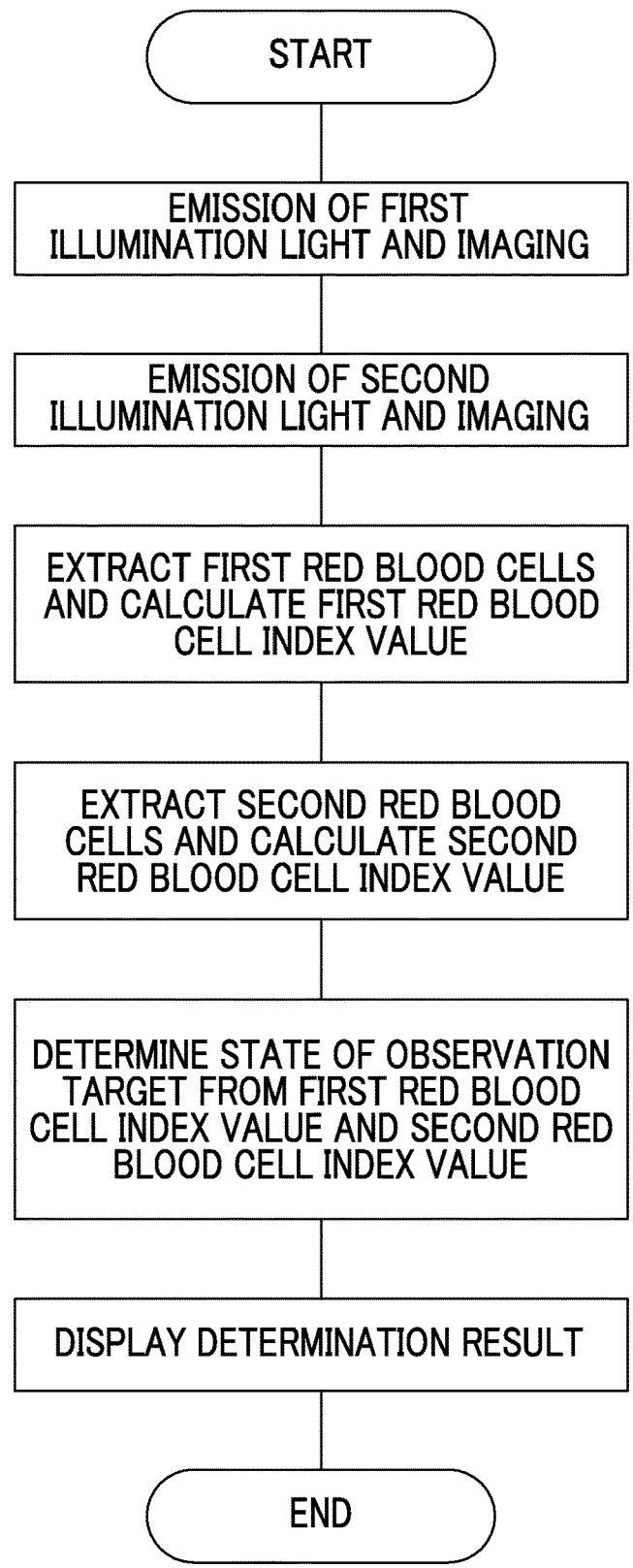
FIG. 7 is a flowchart showing a series of flow in a red blood cell observation mode.

Next, the flow of the red blood cell observation mode will be described with reference to the flowchart shown in FIG. 7. First, an observation target is illuminated with the first illumination light, and the observation target illuminated with the first illumination light is imaged to acquire a medical image. After the emission of the first illumination light and the imaging are completed, the observation target is illuminated with the second illumination light, and the observation target illuminated with the second illumination light is imaged to acquire a medical image.

Then, first red blood cells are extracted from the medical image obtained at the time of emission of the first illumination light and imaging. Based on the extracted first red blood cells, a first red blood cell index value obtained by indexing the visibility of the first red blood cells is acquired. Similarly, second red blood cells are extracted from the medical image obtained at the time of emission of the second illumination light and imaging. Based on the extracted second red blood cells, a second red blood cell index value obtained by indexing the visibility of the second red blood cells is acquired.

Then, the state of the observation target is determined based on the first red blood cell index value and the second red blood cell index value. As the state of the observation target, for example, the disease stage (Mayo0, Mayo1, and Mayo2) of ulcerative colitis is determined. In a case where both the first red blood cell index value and the second red blood cell index value are "0", Mayo0 is determined. In a case where the first red blood cell index value is "1" and the second red blood cell index value is "0", Mayo1 is determined. That is, in a case where both the first red blood cell index value and the second red blood cell index value are "1", Mayo2 is determined. The determination result described above is transmitted to the display control unit 66 and displayed on the monitor 18.

Second Embodiment

In a second embodiment, as one special mode, a gland duct structure observation mode for observing a gland duct structure contained in the observation target by emitting the first illumination light and the second illumination light so as to be switched therebetween is performed. Also in the gland duct structure observation mode, emission of illumination light and imaging of the observation target are performed in the same method as in the red blood cell observation mode.

Figures 8, 9:
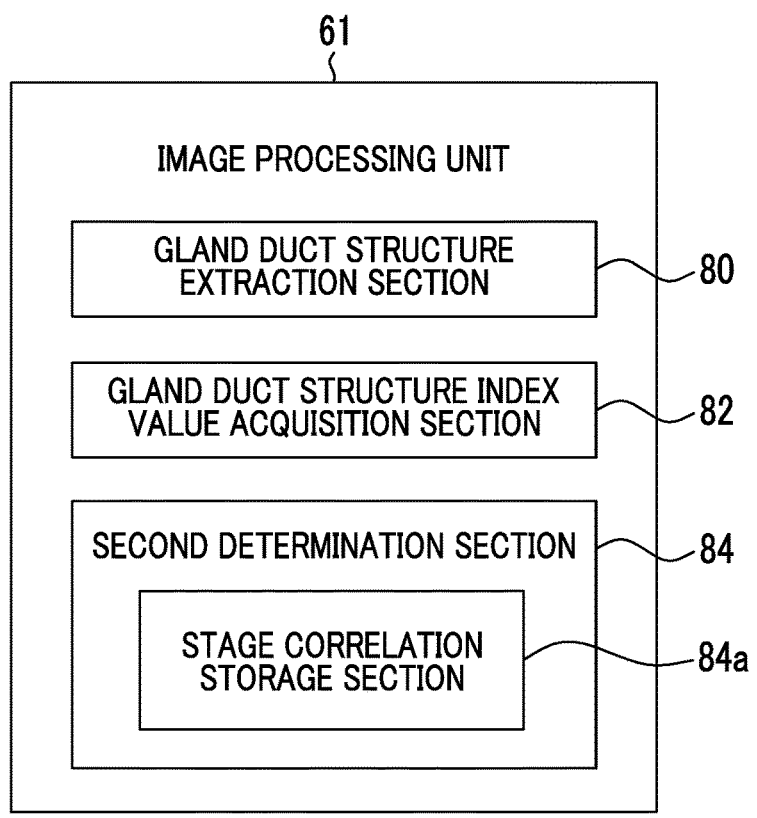
FIG. 8 is an explanatory diagram showing visibility with respect to the degree of irregularity of a gland duct structure for first illumination light and second illumination light.
FIG. 9 is a block diagram showing a function of an image processing unit of a second embodiment.

In the gland duct structure observation mode, visibility with respect to the degree of irregularity of the gland duct structure is different between a case where the observation target is illuminated with the first illumination light and a case where the observation target is illuminated with the second illumination light. As shown in FIG. 8, in a case where the degree of irregularity of the gland duct structure is low, such as a case where gland duct structures are regularly arranged in the observation target, the state of the degree of irregularity of the gland duct structure can be visually recognized ("Visible") in a case where any of the first illumination light and the second illumination light is emitted to the observation target.

In a case where the regularity of the arrangement of gland duct structures slightly collapses in the observation target and the degree of irregularity of the gland duct structure is medium, the state of the degree of irregularity of the gland duct structure can be visually recognized ("Visible") in a case where the first illumination light is emitted to the observation target. On the other hand, in a case where the second illumination light is emitted, the state of the degree of irregularity of the gland duct structure cannot be visually recognized ("Invisible"). In a case where the regularity of the arrangement of gland duct structures greatly collapses in the observation target and the degree of irregularity of the gland duct structure is high as in a case where most of the gland duct structures disappear, the state of the degree of irregularity of the gland duct structure cannot be visually recognized ("Invisible") in a case where any of the first illumination light and the second illumination light is emitted to the observation target.

As shown in FIG. 9, the image processing unit 61 includes a gland duct structure extraction section 80, a gland duct structure index value acquisition section 82, and a second determination section 84 used in the gland duct structure observation mode. The gland duct structure extraction section 80 extracts a first gland duct structure from the medical image obtained at the time of emission of the first illumination light. For extraction of the first gland duct structure, it is preferable to use frequency filtering processing for gland duct structure extraction for extracting the spatial frequency of the gland duct structure. By performing the frequency filtering for gland duct structure extraction, the first gland duct structure is extracted on the up edge. Similarly, a second gland duct structure is extracted from the medical image obtained at the time of emission of the second illumination light. The extraction of the second gland duct structure is also performed in the same manner as the extraction of the first gland duct structure.

The gland duct structure index value acquisition section 82 acquires a first gland duct structure index value relevant to the visibility of the first gland duct structure from the first gland duct structure extracted by the gland duct structure extraction section 80. The first gland duct structure index value is set to two stages of "1" and "0". "1" is a case where the region of the first gland duct structure is equal to or greater than a predetermined area and the first gland duct structure can be visually recognized by the user. "0" is a case where the region of the first gland duct structure is less than the predetermined area and the first gland duct structure cannot be visually recognized by the user. Similarly, the gland duct structure index value acquisition section 82 acquires a second gland duct structure index value, which is obtained by indexing the visibility of the second gland duct structure, from the second gland duct structure extracted by the gland duct structure extraction section 80. The method of acquiring the second gland duct structure index value is the same as in the case of the first gland duct structure index value.

The second determination section 84 determines the state of the observation target based on the first gland duct structure index value and the second gland duct structure index value acquired by the gland duct structure index value acquisition section 82. As in the first embodiment, the second determination section 84 determines the disease stage of ulcerative colitis as the state of the observation target. The disease stage of ulcerative colitis includes three stages of Mayo0 (M0) with a low degree of irregularity of gland duct structures (first disease stage), Mayo1 (M1) with a medium degree of irregularity of gland duct structures (second disease stage in which the disease state is worse than in the first disease stage), and Mayo2 (M2) with a high degree of irregularity of gland duct structures (third disease stage in which the disease state is worse than in the second disease stage).

The correlation between the disease stage and the first gland duct structure index value and the correlation between the disease stage and the second gland duct structure index value are as follows. As shown in (A) of FIG. 10, the first gland duct structure index value indicated by the solid line is "1" in the case of Mayo0, and is "0" in the case of Mayo1 and Mayo2. Therefore, only two stages of Mayo0 and Mayo1, 2 can be determined with the first gland duct structure index value. As shown in (B) of FIG. 10, the second gland duct structure index value indicated by the dotted line is "1" in the case of Mayo0 and Mayo1, and is "0" in the case of Mayo2. Therefore, only two stages of Mayo0, 1 and Mayo2 can be determined with the second gland duct structure index value.

Figures 10, 11:
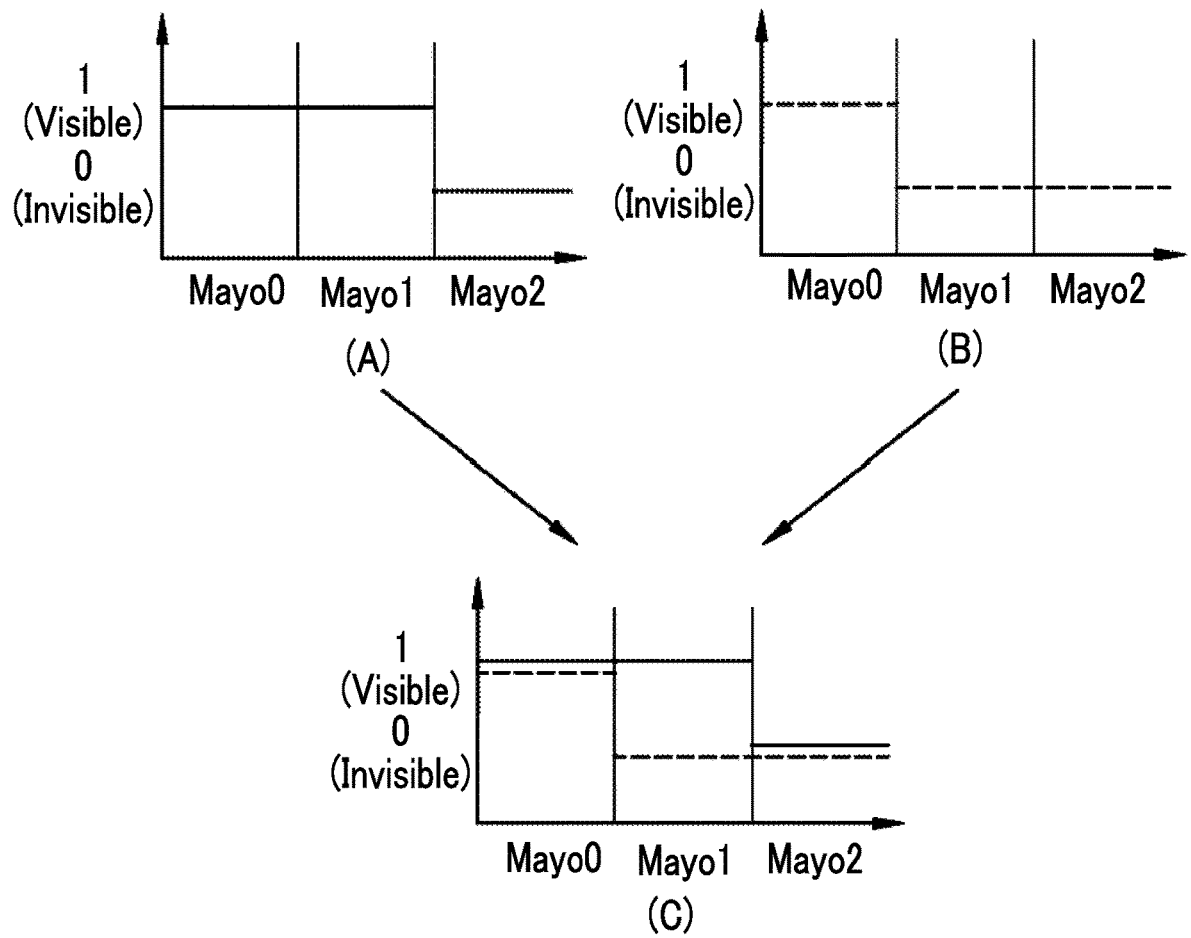
FIG. 10 is an explanatory diagram showing a correlation between the disease stage and a first gland duct structure index value, a correlation between the disease stage and a second gland duct structure index value, and a correlation between the disease stage and the first and second gland duct structure index values.
FIG. 11 is a table showing a stage correlation table in which the correlation between the disease stage and each of the first gland duct structure index value and the second gland duct structure index value is stored.

Therefore, as shown in (C) of FIG. 10, Mayo1, 2, 3 can be determined in three steps by using both the first gland duct structure index value and the second gland duct structure index value. That is, in a case where both the first gland duct structure index value and the second gland duct structure index value are "1", Mayo0 is determined. In a case where the first gland duct structure index value is "1" and the second gland duct structure index value is "0", Mayo1 is determined. In a case where both the first gland duct structure index value and the second gland duct structure index value are "0", Mayo2 is determined. From the above, it is possible to increase the resolution of the disease stage by using a plurality of gland duct structure index values based on a plurality of illumination light beams having different visibilities for a gland duct structure, such as the first illumination light or the second illumination light. In this manner, in a case where the resolution of the disease stage with respect to illumination light to be used is known, it is possible to adjust the number of illumination light beams according to the determination accuracy of the disease stage desired by the doctor.

As shown in FIG. 11, the second determination section 84 includes a stage correlation table 84a in which the above-described correlation between the disease stage and each of the first gland duct structure index value and the second gland duct structure index value is stored. For example, in a case where the first gland duct structure index value is "1" and the second gland duct structure index value is "0", the second determination section 84 determines that the disease stage is "Mayo1" with reference to the stage correlation table 84a. The determination result is transmitted to the display control unit 66 and displayed on the monitor 18.

In the first embodiment, the first red blood cell index value and the second red blood cell index value indicating whether or not red blood cells can be visually recognized are acquired, and the disease stage is determined by combining two of the first red blood cell index value and the second red blood cell index values. However, the disease stage may be determined using other methods. For example, instead of setting the first red blood cell index value to values of two stages of "0" and "1", the first red blood cell index value is set to a variable W1 that changes according to the number of red blood cells extracted from the medical image obtained at the time of emission of the first illumination light. In addition, instead of setting the second red blood cell index value to values of two stages of "0" and "1", the second red blood cell index value is set to a variable W2 that changes according to the number of red blood cells extracted from the medical image obtained at the time of emission of the first illumination light.

Figure 12A:
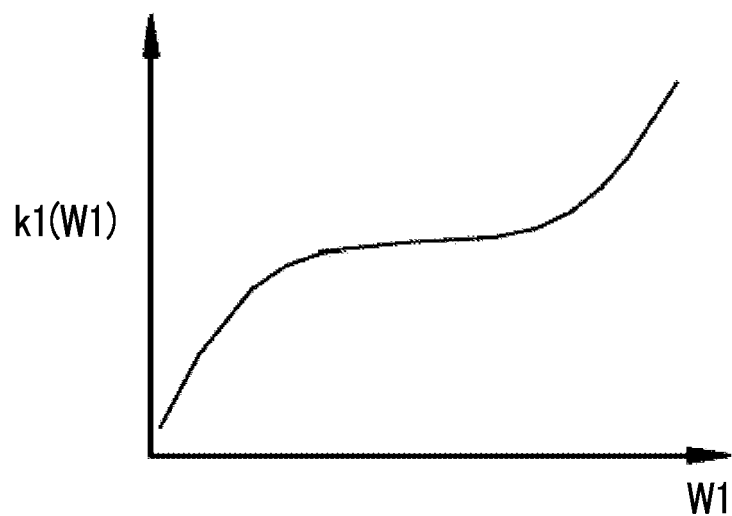
FIG. 12A is a graph showing a weighting coefficient k1 (W1)
Figure 12B:
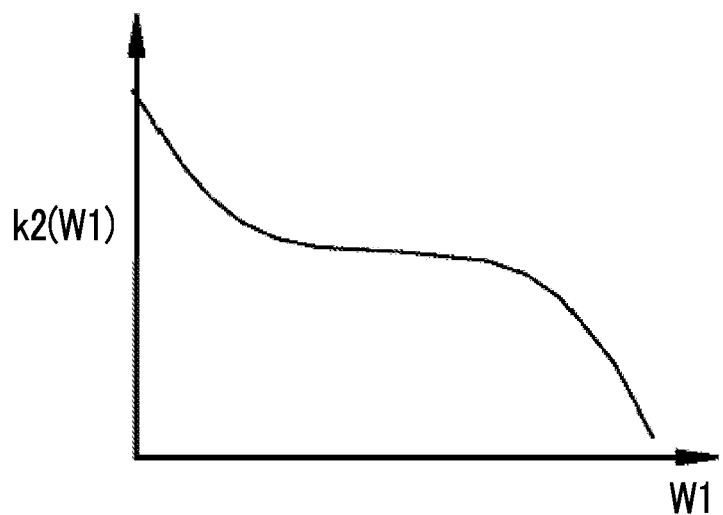
FIG. 12B is a graph showing a weighting coefficient k2 (W2).

A value (k1×W1+k2×W2) obtained by multiplying the variables W1 and W2 by weighting coefficients k1 and k2 and adding up the multiplication results may be set as a third red blood cell index value used for the determination of the disease stage in the first determination section 74. It is preferable that the weighting coefficients k1 and k2 are functions of W1. It is preferable to set k1 (W1) so as to increase as W1 increases as shown in FIG. 12A and set k2 (W1) so as to decrease as W1 increases as shown in FIG. 12B.

Also in the second embodiment, the first gland duct structure index value may be set as a variable Z1 that changes according to the region of the gland duct structure, the second gland duct structure index value may be set as a variable Z2 that changes according to the region of the gland duct structure, and a value (p1×Z1+p2×Z2) obtained by multiplying the variables Z1 and Z2 by weighting coefficients p1 and p2 and adding up the multiplication results may be set as a third gland duct structure index value used for the determination of the disease stage in the second determination section 84.

In the first and second embodiments, the invention is applied to the endoscope system that performs processing on an endoscope image that is one of medical images. However, the invention can also be applied to a medical image processing system that processes medical images other than the endoscope image. The invention can also be applied to a diagnostic support apparatus for performing diagnostic support for a user using a medical image. The invention can also be applied to a medical service support apparatus for supporting the medical service, such as a diagnosis report, using a medical image.

In the embodiment described above, the hardware structures of processing units that execute various kinds of processing, such as the red blood cell extraction section 70, the red blood cell index value acquisition section 72, the first determination section 74, the stage correlation table 74*a*, the gland duct structure extraction section 80, the gland duct structure index value acquisition section 82, the second determination section 84, and the stage correlation table 84*a* included in the image processing unit 61, are various kinds of processors shown below. The various processors include: a central processing unit (CPU) that is a general-purpose processor that functions as various processing units by executing software; a programmable logic device (PLD) that is a processor whose circuit configuration can be changed after manufacture, such as field programmable gate array (FPGA), a dedicated electrical circuit that is a processor having a dedicated circuit configuration for executing various kinds of processing; and the like.

One processing unit may be configured by one of various processors, or may be a combination of two or more processors of the same type or different types (for example, a combination of a plurality of FPGAs or a combination of a CPU and an FPGA). In addition, a plurality of processing units may be configured by one processor. As an example of configuring a plurality of processing units using one processor, first, so represented by a computer, such as a client or a server, there is a form in which one processor is configured by a combination of one or more CPUs and software and this processor functions as a plurality of processing units. Second, as represented by a system on chip (SoC) or the like, there is a form of using a processor for realizing the function of the entire system including a plurality of processing units with one integrated circuit (IC) chip. Thus, various processing units are configured by using one or more of the above-described various processors as a hardware structure.

More specifically, the hardware structure of these various processors is an electrical circuit (circuitry) in the form of a combination of circuit elements, such as semiconductor elements.

EXPLANATION OF REFERENCES

10: endoscope system
12: endoscope
12*a*: insertion part
12*b*: operation unit
12*c*: bending portion
12*d*: distal end portion
12*e*: angle knob
12*f*: forceps inlet
13: zoom operation unit
14: light source device
16: processor device
18: monitor
19: user interface
20: light source unit
20*a*: first illumination light emitting section
20*b*: second illumination light emitting section
20*c*: third illumination light emitting section
20*d*: fourth illumination light emitting section
22: light source control unit
30*a*: illumination optical system
30*b*: imaging optical system
41: light guide
45: illumination lens
46: objective lens
47: zoom lens
48: image sensor
52: central control unit
54: image acquisition unit
56: digital signal processor (DSP)
58: noise reduction section
59: conversion section
61: image processing unit
66: display control unit
70: red blood cell extraction section
72: red blood cell index value acquisition section
74: first determination section
74*a*: correlation table
80: gland duct structure extraction section
82: gland duct structure index value acquisition section
84: second determination section
84*a*: correlation table

What is claimed is:

1. A medical image processing system, comprising:
a light source that emits a plurality of illumination light beams having different wavelength bands and different visibilities for red blood cells; and
a processor configured to:
acquire a plurality of medical images corresponding to respective illumination light beams by imaging an observation target illuminated with the respective illumination light beams;
acquire a red blood cell index value, which is obtained by indexing the visibility of red blood cells, from each of the medical images; and
determine a state of the observation target from the red blood cell index value with reference to a correlation between the state of the observation target and the red blood cell index value,
wherein the plurality of illumination light beams include first illumination light having a center wavelength of 410 nm and second illumination light having a center wavelength of 450 nm,
the processor acquires a first red blood cell index value from a medical image corresponding to the first illumination light, and acquires a second red blood cell index value from a medical image corresponding to the second illumination light, and
the processor determines that there is no precipitation amount of the red blood cells in a case where both the first red blood cell index value and the second red blood cell index value indicate that the red blood cells are not visually recognizable, determines that the precipitation amount of the red blood cells is equal to or less than a specific value in a case where the first red blood cell index value indicates that the red blood cells are visually recognizable and the second red blood cell index value indicates that the red blood cells are not visually recognizable, and determines that the precipitation amount of the red blood cells exceeds the specific value in a case where both the first red blood cell index value and the second red blood cell index value indicate that the red blood cells are visually recognizable.

2. A medical image processing system, comprising:
a light source that emits a plurality of illumination light beams having different wavelength bands and different visibilities for red blood cells; and
a processor configured to:
acquire a plurality of medical images corresponding to respective illumination light beams by imaging an observation target illuminated with the respective illumination light beams;
acquire a red blood cell index value, which is obtained by indexing the visibility of red blood cells, from each of the medical images; and
determine a state of the observation target from the red blood cell index value with reference to a correlation between the state of the observation target and the red blood cell index value,
wherein the plurality of illumination light beams include first illumination light having a center wavelength of 410 nm and second illumination light having a center wavelength of 450 nm,
the processor acquires a first red blood cell index value from a medical image corresponding to the first illumination light, and acquires a second red blood cell index value from a medical image corresponding to the second illumination light, and
the processor determines the state of the observation target based on a third red blood cell index value obtained by weighting the first red blood cell index value and the second red blood cell index value and adding up the weighted first red blood cell index value and the weighted second red blood cell index value.

3. An endoscope system, comprising:
the medical image processing system according to claim 1; and
an endoscope that emits any one of the plurality of illumination light beams to the observation target.

4. A diagnostic support apparatus comprising the medical image processing system according to claim 1.

5. A diagnostic support apparatus comprising the medical image processing system according to claim 2.

6. A medical service support apparatus comprising the medical image processing system according to claim 1.

7. A medical service support apparatus comprising the medical image processing system according to claim 2.

* * * * *